Jan. 24, 1950 W. R. PIERSON, JR Plant Pat. 916
ROSE PLANT
Filed Nov. 24, 1948
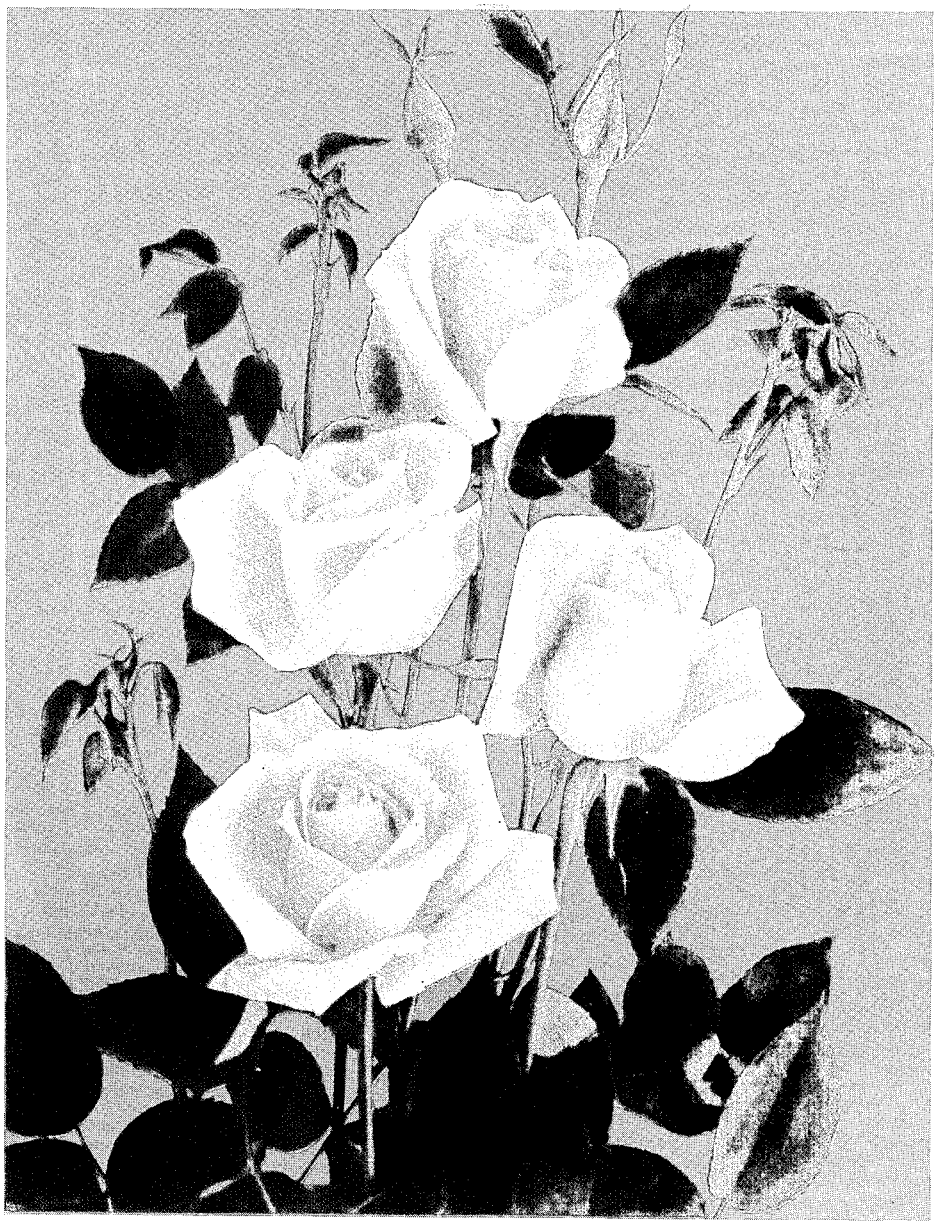
INVENTOR
Wallace R. Pierson, Jr.
By Orville M Kile
Plant Pat. Agt.

Patented Jan. 24, 1950

Plant Pat. 916

UNITED STATES PATENT OFFICE

916

ROSE PLANT

Wallace R. Pierson, Jr., Cromwell, Conn., assignor to A. N. Pierson, Inc., Cromwell, Conn Application November 24, 1948, Serial No. 61,827

1 Claim. (Cl. 47—61)

My present discovery relates to a new and improved variety of hybrid tea rose plant, originating as a sport of the variety Better Times. The sport was discovered by me in our greenhouses a few years ago and has since been propagated through several generations. All of its outstanding characteristics have proved to be permanent.

The growth of this new variety is very vigorous and extremely erect and upright; also very free-breaking, producing many long stems and large flowers. Bud opens pointed and flower is more "perfect" in shape than other similar roses, with no tendency to bullhead, unlike most other sports of the Briarcliff family.

The illustrations making a part of this application show four specimens of the flower of my new variety, together with buds, foliage and stems.

Following is a detailed description of my new variety, in which color plate references indicate Ridgway's Color Standards and Nomenclature.

*The plant*

Growth: Extremely erect and upright, attaining six or seven feet in height. Very free-breaking, producing many long stems.

Blooming habit: Continuous, producing many large flowers.

Stems: Long, straight, strong, Light Elm Green (Plate XVII) tinged with English Red (Plate II); free from thorns except at the base of the stems.

Foliage:

*Leaves.*—Compound, with 3 to 5 leaflets.

*Shape.*—Leaflets oval, with acuminate apex. Margin finely and sharply serrated.

*Size.*—Terminal leaflet is approximately 3 inches long and 1½ inches wide. Lateral leaflets considerably smaller.

*Color.*—Yew Green (Plate XXXI) on upper surface; Malachite Green (Plate XXXII) on under surface. Very young foliage is tinged with Neutral Red (Plate XXXVIII).

*Rachis.*—Slender and smooth.

*Stipules.*—Medium in length and width. Clinging.

*Sepals.*—Light Elm Green (Plate XVII) slightly tinged with red. At least one or two of the five inclined to be foliaceous.

*The flower*

Bud:

*Shape.*—Pointed, continuing pointed throughout its opening. Interior petals are as long as outer ones.

*Opening.*—Lacks any tendency to bullhead.

*Color.*—Approximately Deep Rose Pink (Plate XII) although with considerably more brilliance.

*Size.*—Medium to large.

Bloom:

*Form.*—High-centered, which it retains. Very "perfect" in form, with even petals.

*Petalage.*—From 30 to 38 during the summer months; a few more in the winter when grown under glass.

*Size.*—Approximately 5 inches in diameter, as an all-year average.

*Color.*—Rose Pink to Deep Rose Pink (Plate XII), with an added brilliance not possible to show in the color guide or paintings. This color is maintained until the flower dies.

*Fragrance.*—Slight but very pleasing.

*Lasting quality.*—Very good.

*Behavior.*—Petals cling when dead.

Reproductive organs: Many stamens and pistils form the center of the flower but are seldom visible because of the high-centered form of the flower.

*Comparison*

The known variety most like my new variety is Happy Days (Plant Patent No. 144), which is a sport of Briarcliff. However the two varieties differ principally in the following points.

1. My variety does not bullhead while other sports of the Briarcliff family, including Happy Days, very definitely have the tendency to bullhead.

2. Growth of my new variety is more vigorous and erect.

3. My variety is much more free-breaking, producing more stems.

4. My variety produces more flowers during the growing season.

5. The flower of my variety is much lighter in color.

6. The flower of my variety is more "perfect" in form.

7. The flower of my variety has more petals and is larger.

8. The bud of my variety is much more pointed.

Having thus disclosed my discovery, I claim:

The new and distinct variety of hybrid tea rose plant of the Briarcliff family, substantially as herein shown and described, characterized particularly by its very upright, free and vigorous growth; its many long, sturdy stems; its habit of breaking freely and of producing large numbers of stems and flowers; its pointed buds; and its flowers of "perfect" form, brilliant light pink color and lack of any tendency to bullhead.

WALLACE R. PIERSON, JR.

No references cited.